United States Patent [19]

Currie

[11] Patent Number: 5,140,102
[45] Date of Patent: Aug. 18, 1992

[54] PENTADECAPEPTIDE, GUANYLIN, WHICH STIMULATES INTESTINAL GUANYLATE CYCLASE

[75] Inventor: Mark G. Currie, St. Charles, Mo.

[73] Assignee: Monsanto Company, St. Louis, Mo.

[21] Appl. No.: 764,461

[22] Filed: Sep. 23, 1991

[51] Int. Cl.$^5$ ................................................ C07K 7/08
[52] U.S. Cl. ....................................................... 530/326
[58] Field of Search .......................................... 530/326

[56] References Cited

PUBLICATIONS

Schultz et al., Cell, 63, 941–948 (1990).
Yoshimura et al., FEBS Lett., 181, 138–142 (1985).

Primary Examiner—Merrell C. Cashion, Jr.
Assistant Examiner—Susan M. Perkins
Attorney, Agent, or Firm—Scott J. Meyer

[57] ABSTRACT

A novel pentadecapeptide is disclosed which is useful for the control of intestinal fluid absorption and that has the following amino acid sequence Pro—Asn—Thr—Cys—Glu—Ile—Cys—Ala—Tyr—Ala—Ala—
1                               5                              10
Cys—Thr—Gly—Cys.
                15

1 Claim, 4 Drawing Sheets

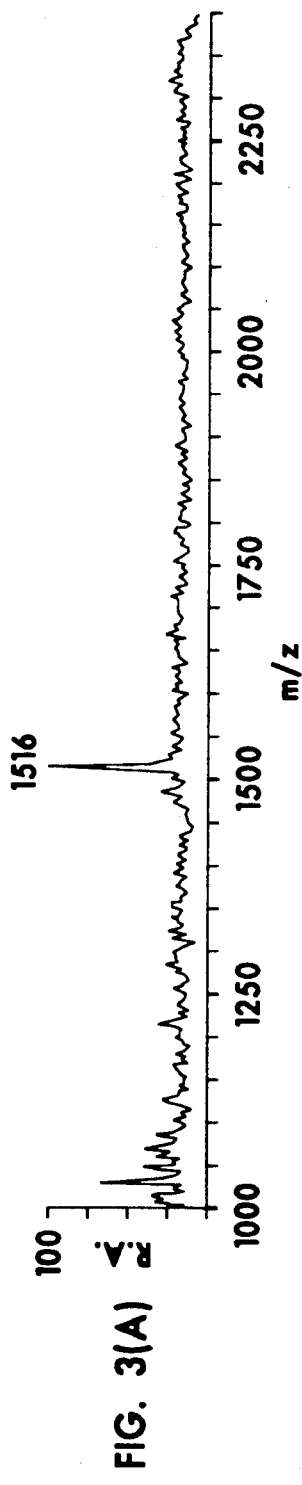
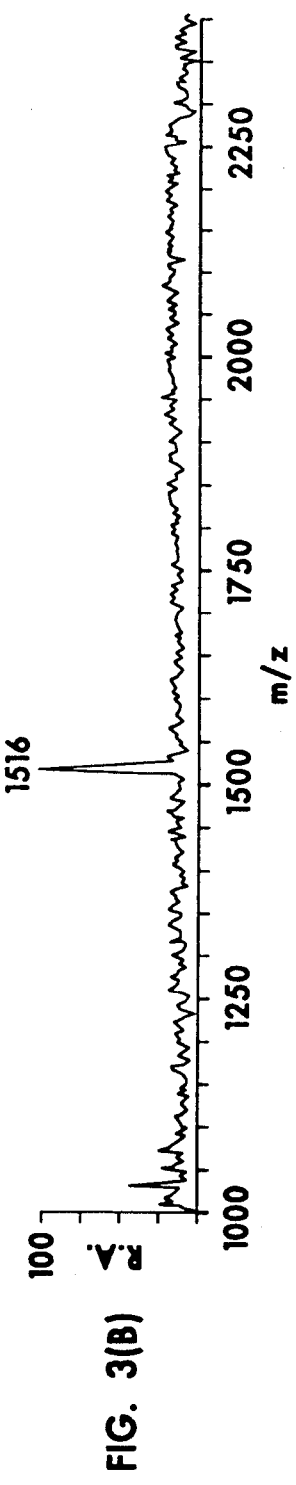
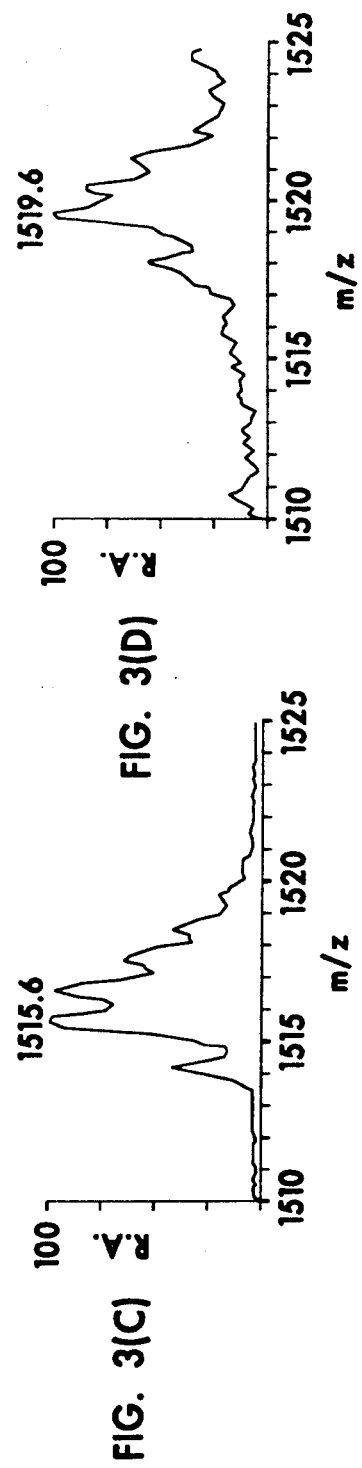
FIG. 3(A)
FIG. 3(B)
FIG. 3(C)
FIG. 3(D)

PENTADECAPEPTIDE, GUANYLIN, WHICH STIMULATES INTESTINAL GUANYLATE CYCLASE

BACKGROUND OF THE INVENTION

This invention relates to a novel peptide and, more particularly, to a pentadecapeptide that is an endogenous regulator of intestinal guanylate cyclase.

Guanylate cyclase is composed of a group of proteins that share structural characteristics relative to the enzymatic function of producing cyclic GMP, but differ quite remarkably in their selective activation by ligands. The three major forms of guanylate cyclase are the soluble, particulate, and intestinal (cytoskeletal-associated particulate or STa-sensitive) with each of these forms regulated by different ligands (1, 2). Activation of the soluble guanylate cyclase occurs in response to nitric oxide (EDRF), while activation of the particulate enzyme occurs in response to the natriuretic peptides (atrial natriuretic peptide, brain natriuretic peptide, and C-type natriuretic peptide) (1, 2). An endogenous activator of the intestinal guanylate cyclase has not previously been identified, however the heat stable enterotoxin from E. coli is known to selectively activate this form of the enzyme (3,4). This form of the enzyme is predominantly found in the intestinal epithelial cells with the largest number of receptors oriented towards the lumen (1,2). Recently, the intestinal form of guanylate cyclase has been cloned and expressed from rat small intestinal mucosa (5). This enzyme is characterized by an extracellular receptor binding region, a transmembrane region, an intracellular protein kinase-like region and a cyclase catalytic domain (5).

Pathogenic strains of E. coli and other bacteria produce a family of heat stable entertoxins (STs) that activate intestinal guanylate cyclase. STs are acidic peptides 18-19 amino acids in length with six cysteines and three disulfide bridges that are required for full expression of bioactivity (6). The increase of intestinal epithelial cyclic GMP elicited by STs is thought to cause a decrease in water and sodium absorbtion and an increase in chloride secretion (7, 8). These changes in intestinal fluid and electrolyte transport then act to cause secretory diarrhea. In developing countries, the diarrhea due to STs is the cause of many deaths, particularly in the infant population (9). STs are also considered to be a major cause of traveler's diarrhea in developed countries (10). STs have also been reported to be a leading cause of morbidity in domestic animals (11).

BRIEF DESCRIPTION OF THE INVENTION

In accordance with the present invention a novel pentadecapeptide is provided which has the following amino acid sequence.

Pro—Asn—Thr—Cys—Glu—Ile—Cys—Ala—Tyr—Ala—Ala—
1                    5                     10
Cys—Thr—Gly—Cys
15

This peptide [SEQ ID NO:1], also referred to herein as guanylin, has been isolated from the rat jejunum and has been chemically synthesized by solid phase peptide synthesis. In its oxidized active biologic form, the novel pentadecapeptide has two disulfide bridges, one between cysteine residues at positions 4 and 12 and the other between cysteine residues at positions 7 and 15.

The pentadecapeptide of this invention has been both isolated and chemically synthesized in a homogeneously purified form which did not exist in the rat jejunum from which it was initially obtained. That is, it has been prepared in a form which is essentially free of other low molecular weight peptides, and free from higher molecular weight material and other cellular components and tissue matter. This novel pentadecapeptide has physiological characteristics which suggest that it is important to medical science in the study of regulators of guanylate cyclase. In particular, the novel pentadecapeptide of this invention is an endogenous stimulator of intestinal guanylate cyclase. It has been found to stimulate increases in cyclic GMP levels in a manner similar to the STs. As such regulator, it is useful for the control of intestinal absorption. It has potential to regulate intestinal fluid and electrolyte transport. This pentadecapeptide also has been found to displace heat stable enterotoxin binding to cultured T84 human colon carcinoma cells. This cell line is known to selectively respond to the toxin in a very sensitive manner with an increase in intracellular cyclic GMP.

The pentadecapeptide, guanylin, has been further demonstrated to act in an isolated intestinal rat preparation to stimulate an increase in short circuit current. This action is believed to be the physiologic driving force for eliciting chloride secretion and ultimately decreased water absorption. The guanylin may thus act as a laxative and be useful in patients suffering from constipation, e.g. cystic fibrosis patients who suffer with severe intestinal complications from constipation.

DETAILED DESCRIPTION OF THE INVENTION

While the specification concludes with claims particularly pointing out and specifically claiming the subject matter regarded as forming the present invention, it is believed that the invention will be better understood from the following detailed description of preferred embodiments taken in conjunction with the accompanying drawings in which:

FIG. 1 is a graphical representation which shows the effect of tissue extracts from various tissues on T84 cyclic GMP levels. Acid extracts were prepared from 1 g of tissue, and 10% of total of the extracts were applied to isobutylmethylxanthine (IBMX) treated cells. Cyclic GMP was measured as described in the Methods section, hereinafter.

FIG. 3 shows the electrospray mass spectra of native guanylin (A) and synthetic guanylin (B), both contain the peptide (M+H)+ at m/z 1516. Comparison of the mass spectra of oxidized (C) and reduced (D) native guanylin shows the reduced peptide to be 4 amu higher in mass, which indicates the presence of two disulfide bonds in native guanylin.

FIG. 4 is a graphical representation which shows the time course (A) and concentration-response (B) effect of guanylin on cyclic GMP levels in T84 cells. In the time course test, T84 cells were treated with $10^{-8}$M guanylin. For the concentration response the cells were incubated with varying concentrations of guanylin for 30 min. Cells for both tests were treated with 1 mM IBMX.

Figure 5:
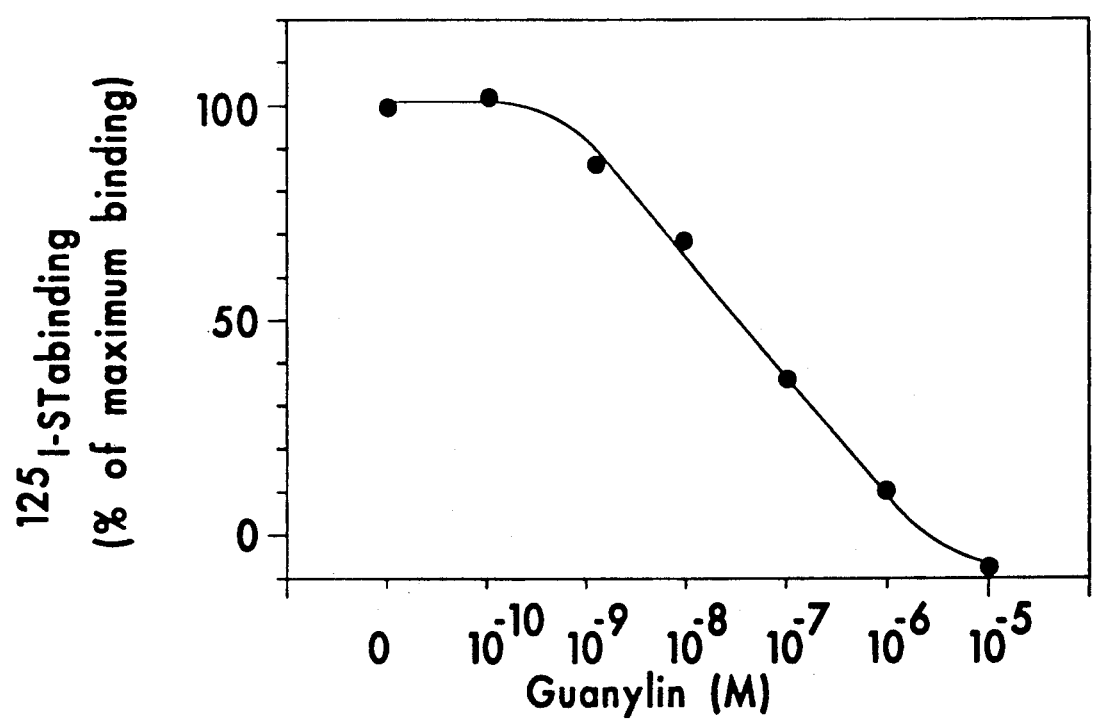

FIG. 5 is a graphical representation which shows the displacement of $^{125}$I-STa specific binding from T84 cells by guanylin. Cells were incubated for 30 min at 37° C. with labeled STa and varying concentrations of guanylin. Specific bound (%) was determined by dividing the specific $^{125}$I-STa bound at each concentration of guanylin by the specific $^{125}$I-STa bound in the absence of guanylin. Each point represents the mean of triplicates.

References parenthetically cited herein are listed hereinbelow.

The novel peptide of this invention can be prepared by known solution and solid phase peptide synthesis methods.

In conventional solution phase peptide synthesis, the peptide chain can be prepared by a series of coupling reactions in which the constituent amino acids are added to the growing peptide chain in the desired sequence. The use of various N-protecting groups, e.g. the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoracetate) and cyanogen bromide, and reaction in solution with isolation and purification of intermediates is well-known classical peptide methodology.

The preferred peptide synthesis method follows conventional Merrifield solid-phase procedures. See Merrifield, *J. Amer. Chem. Soc.* 85, 2149-54 (1963) and *Science* 150, 178-85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or, preferably, p-methylbenzhydrylamine polymer for synthesizing peptide amides. This method conveniently simplifies the number of procedural manipulations since removal of the excess reagents at each step is effected simply by washing the polymer.

The acyl group on the N-terminus is conveniently introduced by reaction of an alkanoic anhydride with the peptide on the solid support after deprotection with TFA.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology*, 32, pp. 221-296, F. F. Nold, Ed., Interscience Publishers, New York, 1969; and Erickson and Merrifield, *The Proteins*, 1 Vol. 2, p. 255 et seq. (ed. Neurath and Hill), Academic Press, New York, 1976.

In order to further illustrate the invention, the following exemplary laboratory preparative work was carried out. However, it will be appreciated that the invention is not limited to these examples or the details described therein.

EXAMPLE 1

Materials and Methods

Cell Culture

A cultured human colon carcinoma cell line (T84) was obtained from the American Type Culture Collection (Rockville, Maryland) (ATCC No. CCL 248) at passage 52. Cells were grown to confluency in 24-well culture plates with a 1:1 mixture of Ham's F12 medium and Dulbecco's modified Eagle's medium (DMEM), supplemented with 10% fetal calf serum, 100 IU/ml penicillin, and 100 μg/ml streptomycin. Cells were used at passages 54-60.

Cyclic GMP determination

Monolayers of T84 cells in 24-well plates were washed twice with 1 ml/well DMEM, then incubated at 37° C. for 10 min with 0.5 ml DMEM containing 1 mM isobutylmethylxanthine, a phosphodiesterase inhibitor. Agents and fractions were then added for the indicated time as described in the results section, below. The media was then aspirated and the reaction terminated by the addition of ice cold 0.5 ml of 0.1N HCl. Aliquots were then evaporated to dryness under nitrogen and then resuspended in 5 mM sodium acetate buffer, pH 6.4. The samples were then measured for cyclic GMP by conventional RIA as described by Steiner et al. (12).

Purification of Guanylin

Rat jejunums that were flushed of luminal contents with 50 ml of saline and immediately placed on dry ice were obtained from Bioproducts for Science (Indianapolis, IN). The jejunums were thawed, minced, and boiled for 10 min in 1M acetic acid. The extract was centrifuged at 20,000 g for 20 min at 4° C. The resulting supernatant was filtered and applied to a C-18 sep pak (Waters, Milford, MA). The column was washed with 10% acetonitrile, 0.1% trifluoroacetic acid (TFA) and eluted with 60% acetonitrile, 0.1% TFA. The eluted peptide fraction was lyophilized and resuspended in 50 ml of distilled water containing 0.8% ampholytes, pH range 3-10, and applied to a preparative isoelectric focusing cell (Rotofor, Bio-Rad, Richmond, CA). The sample was focused for 150 min at 12 Watts constant power. The fractions were harvested, pH determined, and bioassayed. The active fractions which focused around pH 3.8, were then refocused under similar conditions and the resulting active fractions were lyophilized. The sample was then resuspended in 1 ml of 10% acetonitrile, 0.1% TFA and applied to a C-18 semi-preparative HPLC column (Vydac, Hesperia, CA) and run at a rate of 3 ml/min. The following gradient was used to fractionate the sample: 10% acetonitrile, 0.1% TFA to 30% acetonitrile, 0.1% TFA in 180 min. The active fraction was determined by bioassay and lyophilized. The sample was resuspended in 1 ml of 10% acetonitrile, 0.1% TFA and applied to a phenyl analytical HPLC column (Vydac, Hesperia, CA). The conditions for elution were similar to that described above for the semi-preparative column except the rate of flow as 1 ml/min. The active fraction was lyophilized and then resuspended in 1 ml of 10% acetonitrile, 0.1% TFA. The sample was then applied to a C-18 analytical HPLC column (VYDAC, Hesperia, CA) and eluted according to the above description for the phenyl column. The active fraction was identified by bioassay and lyophilized. The sample was reconstituted in 1 ml of 10% acetonitrile, 0.1% TFA and reapplied to the analytical C-18 column and eluted by a gradient of 10% acetonitrile, 10 mM ammonium acetate to 30% acetonitrile, 10 mM ammonium acetate in 180 min. The active fraction was lyophilized and reconstituted in 0.05 ml of 0.1% TFA. The sample was then applied to a C-8 microbore column and eluted by an increasing gradient of 0.33%/min of acetonitrile, 0.1% TFA.

N-terminal protein sequence analysis

Automated Edman degradation chemistry was used to determine the $NH_2$-terminal protein sequence. An Applied Biosystems, Inc. model 470A gas phase sequence (Foster City, CA) was employed for the degradations (13) using the standard sequencer cycle, 03RPTH. The respective PTH-aa derivatives were identified by RP-HPLC analysis in an on-line fashion employing an Applied Biosystems, Inc., Model 120A PTH Analyzer fitted with Brownlee 2.1 mm I.D. PTH-C18 column. On-sequencer pyridylethylation was performed as outlined by Kruft et al. (14). The PTH derivative of pyridylethylcysteine was identified by HPLC as eluting slightly prior to PHT derivatives of methionine.

Electrospray Mass Spectrometry

Individual samples of native and synthetic guanylin were purified by microbore C-8 reversed-phase HPLC (Brownlee Aquapore RP-300 7 micron column, P. J. Cobert, St. Louis, MO) and eluting fractions of the peptides were collected and concentrated to approximately 8 pmol/$\mu$L for mass-analysis. Sample solutions were introduced to the mass spectrometer via injection into a stream of acetonitrile:water:trifluoroacetic acid (1000:1000:1, v:v:v), which continuously flowed to the mass spectrometer at a flow of 10 $\mu$L/min. Three microliters of each of the concentrated guanylin samples were injected to obtain the results that are set forth below.

A Sciex API III triple-quadrupole mass spectrometer (Thornhill, Ontario, Canada) equipped with an atmospheric pressure ion source was used to sample positive ions produced from an electrospray interface (15) that was maintained at a potential difference of 3 kV with respect to the entrance of the mass spectrometer. Mass-analysis of sample ions was accomplished by scanning the first quadrupole in 1 amu increments from 1000-2400 amu in approximately 3 sec., and passing mass-selected ions through the second and third quadrupoles operated in the rf-only mode, to the multiplier, which was operated in the pulse-counting mode. For maximum sensitivity, the mass resolution of the quadrupole mass analyzer was set so that ion signals were approximately 2 amu wide at half peak height, but the centroid of the ion signal still represented the correct mass of the ion. Mass spectra of the guanylin samples were averaged over all of the scans that were acquired during elution of the 3 $\mu$L sample solution.

Binding Assay $^{125}$I-STa was prepared by the conventional Iodogen method (16). T84 cell monolayers were washed twice with 1 ml of DMEM, then incubated for 30 min at 37° C. in 0.5 ml DMEM with $^{125}$I-STa (100,000 cpm/well) and either guanylin or 100 nM STa. The cells were then washed 4 times with 1 ml of DMEM and solubilized with 0.5 ml/well 1 N NaOH. This volume was transferred to tubes and assayed for radioactivity by a gamma counter. Results are expressed as the percentage of specific bound.

Chemical synthesis of Guanylin

Guanylin was synthesized by the conventional solid-phase method (17) with an Applied Biosystems 430A peptide synthesizer on Cys(4-$CH_3$Bzl)-$OCH_2$-Pam Resin using double coupling cycles to ensure completion at each step. Coupling was effected with preformed symmetrical anhydride of t-butoxycarbonylamino acids (Applied Biosystems), and peptides were cleaved from the solid support in hydrogen fluoride, dimethylsulfide, anisole and p-thiocresol used at a 8/1/1/0.5 ratio (v/v/v/w) at 0° C. for 60 min. Peptides were cyclized using dimethylsulfoxide as described by Tam et al. (18). Peptides were purified by successive reverse-phase chromatography on a 45×300 mm Vydac C18 column and on a 19×150 mm $\mu$Bondapak C18 column, using a gradient of 10-30% acetonitrile in 0.5% trifluoroacetic acid. The structures and purity of the synthetic peptides were verified by fast atom bombardment/mass spectroscopy or thermospray/mass spectroscopy, amino acid analysis, and gas-phase sequence analysis.

RESULTS

Figure 1:
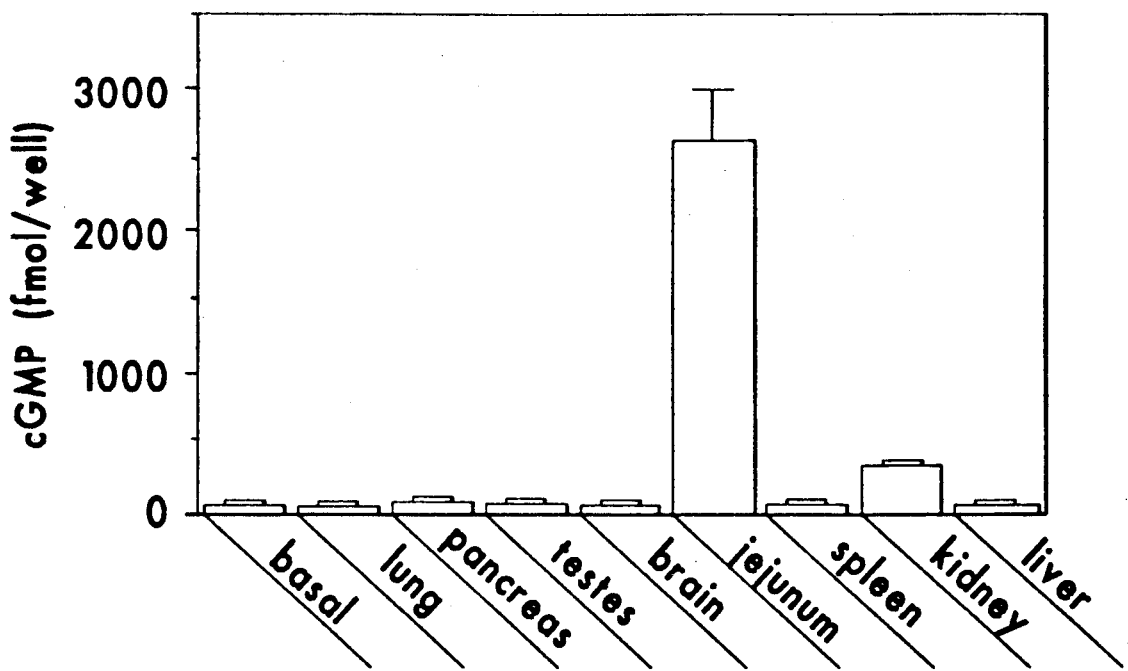

Initial characterization of the T84 cell response indicated that these cells were very sensitive to STA (limit of detection $10^{-10}$M) and displayed a remarkable range with a maximal response eliciting a greater than 10,000 fold increase in cyclic GMP. Furthermore, an effect on cyclic GMP levels with $10^{-3}$ M sodium nitroprusside or $10^{-6}$ M atrial natriuretic peptide was not detected, suggesting that the T84 serves as a selective bioassay for agents that activate the intestinal guanylate cyclase. A survey of acid boiled and extracted rat tissues for the ability to increase T84 cell cyclic GMP levels indicated that both the jejunum and kidney possessed this activity while liver, brain, pancreas, spleen, lung, and testes lacked bioassayable activity (FIG. 1). The relative specific activity appeared to be greater in the intestinal tissue and therefore this tissue was utilized for purification of the active material. One possibility in the early stages of purification was that the active material was a STs. However, examination of embryonic intestine which is bacteria free indicated that this tissue also possessed bioactive material.

Figure 2:
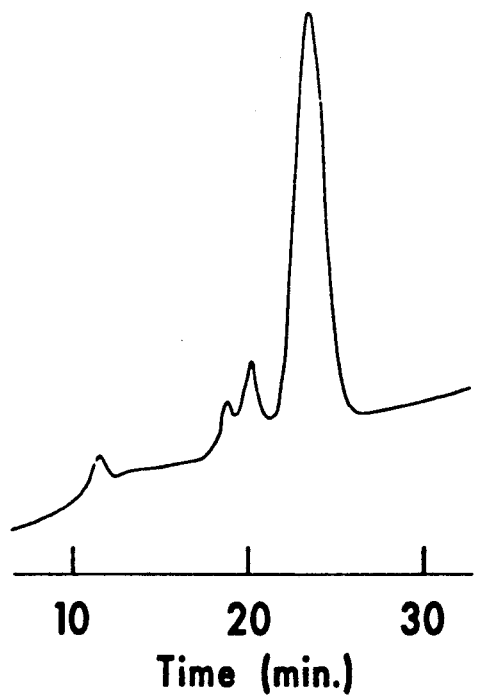
FIG. 2 shows the elution profile of the final purification of guanylin by C8 reverse phase on microbore HPLC. Peaks were collected by hand and measured for activity The active peak is indicated by shading with 3% of the fraction giving a 10-fold increase in cyclic GMP.

Purification of the jejunal bioactivity was accomplished by the processing scheme described in the methods, hereinbefore. Briefly, following acid boiling and extraction by a C18 reverse-phase matrix, the material was fractionated on a preparative isoelectric focusing cell which resulted in a 200-fold purification and indicated that the isoelectric point was about 3.8. Refocusing of the active fraction resulted in a further 5-10 fold purification. The active fraction was then purified to homogeneity by applying it to a series of reverse-phase HPLC steps; which included a semi-preparative C18 column, a phenyl column, two runs on a C18 column utilizing different ion-pairing reagents, and final purification on a microbore C8 column (FIG. 2).

Preliminary tests indicated that the material was a low molecular weight peptide, thus, the material was initially subjected to N-terminal protein sequence analysis and ultimately to electrospray mass spectrometry. The combination of the data derived from these two techniques yielded the complete consensus sequence for guanylin as shown above. The N-terminal sequence through 14 places was determined by two independent gas phase sequencing tests. The initial results yielded a sequence in which no PTH-aa derivative was observed at positions 4, 7, and 12. Since cysteine residues can not be positively identified during gas phase sequencing without reduction and alkylation, the lack of a PTH-aa derivative at these positions indicate the presence of cysteine residues. For complete verification, the putative cysteine residues of guanylin were pyridylethylated and the peptide was resequenced. The subsequent N-terminal gas phase sequence analysis verified cysteine residues at positions 4, 7, and 12. Further primary structure information was obtained by electrospray mass spectrometry. The electro spray mass spectrum of native guanylin (FIG. 3A) contains an ion signal at m/z 1516 that corresponds to the protonated peptide. This mass assignment is 103 amu higher in mass than the mass that would be expected for a peptide with the sequence that was obtained by gas-phase sequencing analysis. Since the first 14 N-terminal amino acids were already determined, the 103 amu mass addition was thought to result from an additional disulfide-linked cysteine or threonine at the C-terminus. Reduction of the disulfide bonds of guanylin with dithiothreitol resulted in a 4 amu increase in molecular weight of the peptide indicating that it contains two disulfide bonds. Therefore, since only three cysteines are contained in the original 14 N-terminal amino acids, the 103 amu difference has to result from an additional C-terminal cysteine that is disulfide-linked to one of the three cysteines in the guanylin sequence. The resulting full amino acid sequence of the peptide was compared with all other proteins in the Gen Bank by a computer based search. This search revealed that guanylin has homology with the STs. The highest percent identity was found between a 12 amino acid overlap of guanylin and P01560 *E. coli* heat stable enterotoxin (19). The major difference between guanylin and the STs is that guanylin possesses 4 cysteines with 2 disulfide-linked bridges while all of the STs have 6 cysteines with 3 disulfide-linked bridges.

Figure 4A:
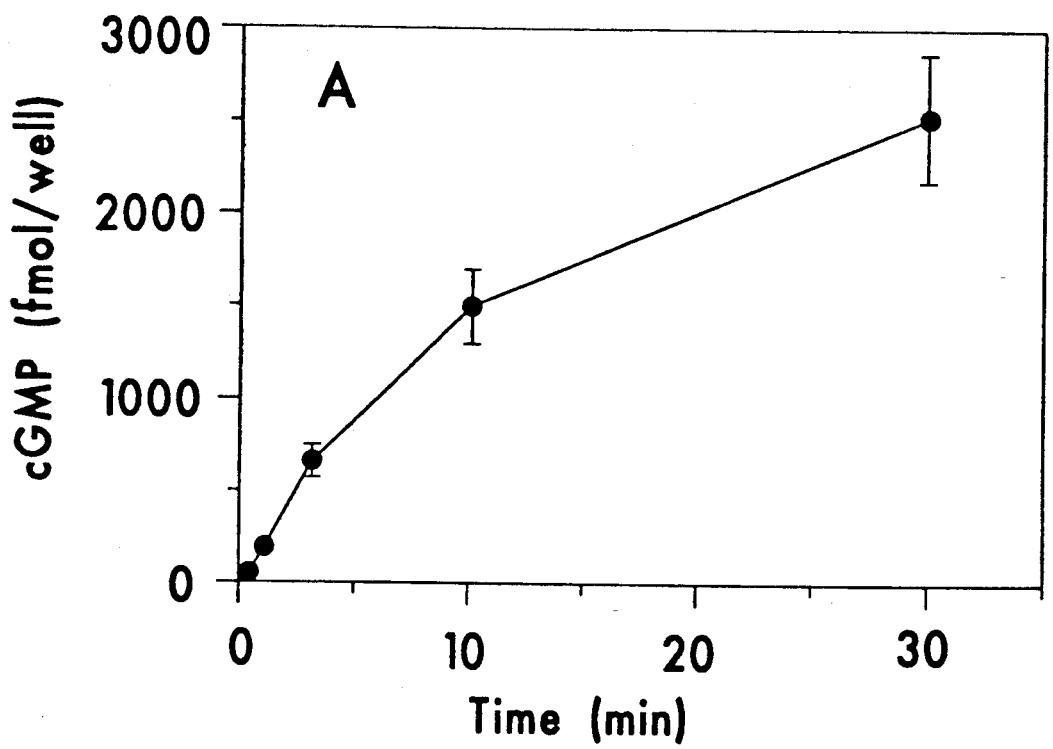
Figure 4B:
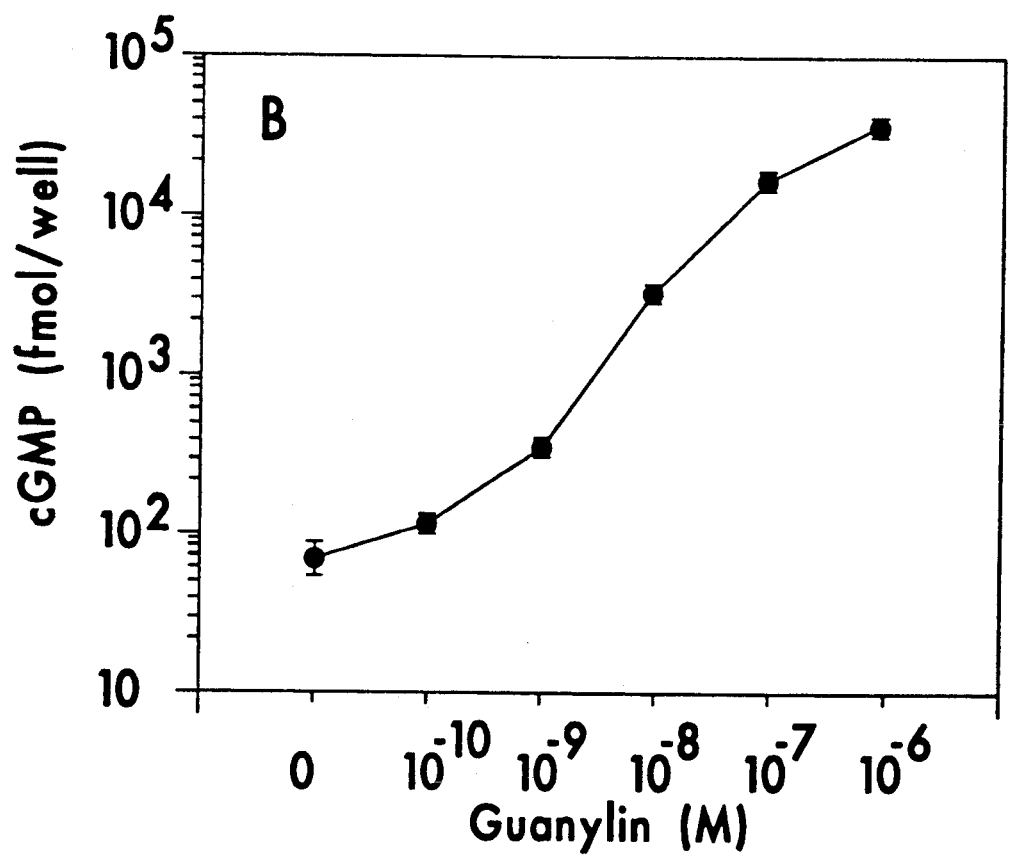

Chemical synthesis of the sequence of guanylin following cyclization resulted in three major fractions of synthetic peptides by HPLC analysis. All of these showed the same M+H mass units as purified guanylin (1516) by mass spectroscopic analysis. However, only one of these fractions exhibited potent bioactivity in a manner similar to native guanylin in the T84 cell bioassay. This peak also possessed a similar retention time on HPLC when compared to native guanylin. Since guanylin has four cysteine residues, the three fractions of synthetic guanylin represented the three possible different disulfide bridge alignments. Bioactive synthetic guanylin stimulated increases in cyclic GMP levels of T84 cells that were both time and concentration dependent. Guanylin ($10^{-8}$ M) was observed to cause a marked elevation of cyclic GMP by 1 min that progressively increased through 30 min (FIG. 4A). Examination of the concentration-response curve shows that guanylin elicited an increase in cyclic GMP at $10^{-10}$ M concentration and this response was observed to continue to increase through the range of concentrations tested (FIG. 4B). To test the effect of treatment of reducing agents on the bioactivity of guanylin, the effect of a 30 min pretreatment of the peptide with 1 mM dithiothreitol (DTT) was tested. The basal level of cyclic GMP for this test was $16\pm5$ fm/well with the addition of guanylin ($10^{-8}$ M) for 30 min the level increased to $282\pm50$ fm/well; however, following the pretreatment of the peptide with DTT the effect of the peptide on cyclic GMP was almost completely abolished ($25\pm5$ fm/well). This action of DTT does not appear to be a direct effect of this reducing agent on guanylate cyclase since treatment of the cells with 10 $\mu$M DTT (final concentration of DTT that the cells were exposed to in the test) failed to affect their responsiveness. Finally, the ability of guanylin to displace specifically bound $^{125}$I-STa from T84 cells was tested. In this test, guanylin caused a concentration-dependent displacement of labeled STa from the T84 cells (FIG. 5).

EXAMPLE 2

This example illustrates the effect of guanylin on colonic ion transport.

Preparation of Intestinal Tissues

Male Sprague-Dawley rats (200-300 g., Charles River Breeding Laboratories, Wilmington, MA) were maintained on a standard laboratory diet and allowed free access to food and water before they were sacrificed by $CO_2$ asphyxiation. The proximal colon was excised and placed immediately in oxygenated modified Krebs-Ringer buffer solution of the following composition (millimolar): NaCl, 120.2; KCl, 5.9; $CaCl_2$, 2.5; $MgCl_2$, 1.2; $NaH_2PO_4$, 1.2; $NaHCO_3$, 25; and glucose, 11.1. The tissue was stripped of its underlying muscle layers by blunt dissection; the resulting preparation consisted of only mucosa and submucosa. Adjacent tissues were then mounted as flat sheets on pins between two Ussing half-chambers (World Precision Instruments, Inc., New Haven, CT) having the area of 0.64 $cm^2$ and bathed on both sides by 5 ml of buffer solution, circulated by gas lift and maintained at 37° C. by water-jacketed reservoirs. The solution was gassed continuously with 5% $CO_2$ in $O_2$ and maintained at pH 7.4.

Electrical measurements were monitored with an automatic voltage clamp (TR100-F, JWT Engineering, Overland Park, KS). Direct connecting voltage and current passing electrodes (World Precision Instruments, Inc.) were utilized to measure transepithelial potential difference (PD) and short-circuit current (Isc). Transepithelial PD was measured periodically and tissue resistance ($R_T$) was calculated from Ohm's law. Isc was recorded continuously on a Gould model 2800S recorder (Gould Inc., Cleveland, OH). Tissues were equilibrated under short-circuit conditions until Isc had stabilized (usually 30-45 min). Basal $R_T$ values averaged $92\pm8$ ohm·$cm^2$ 30 min after mounting.

Effect of Guanylin on Isc

Guanylin evoked an increase in Isc immediately upon mucosal (luminal) addition. The response was concentration dependent over a range of 0.01 $\mu$M–1.0 $\mu$M; the $EC_{50}$ value ($X\pm S.E.$) was determined to be $0.162\pm0.026$ $\mu$M and the maximal response was $37\pm13$ $\mu$A/$cm^2$ (n=4 animals).

Various other examples will be apparent to the person skilled in the art after reading the present disclosure without departing from the spirit and scope of the invention. For example, it will be appreciated that pharmaceutically acceptable salts, esters and amides of the novel pentadecapeptide which do not adversely or detrimentally affect its biological activity as defined herein are also included within the scope of the invention. It is intended that all such other examples be included within the scope of the appended claims.

REFERENCES

1. Singh, S. Lowe, K. G., Thorpe, D. S. Rodriquez, H., Kuang, W.-J., Dangott, L. J., Chinkers, M., Goeddel, D. B , and Garbers, D. L. (1988) *Nature* 334, 708-712.
2. Waldman, S. A., and Murad, F. (1987) *Pharmacological Reviews* 39, 163-196.
3. Field, M., Graf, L. H., Laird, W. J., and Smith, P. L. (1978) *Proc. Natl. Acad. Sci. USA* 75, 2800-2804.

4. Guerrant, R. L., Hughes, J. M., Chang, B., Robertson, D. C., and Murad, F. (1980) *J. Infect. Dis.* 142, 220–228.
5. Schulz, S., Green, C. K., Yuen, P. S. T., and Garbers, D. L. (1990) *Cell* 63, 941–948.
6. Yoshimura, S., Ikemura, H., Watanabe, H., Aimoto, S., Shimonishi, Y., Hara, S., Takeda, T., Miwatani, T., and Takeda, Y. (1985) *FEBS Letters* 181, 138–142.
7. Field, M., Rao, C. M., and Chang, E. /B. (1980) *New England J. Med.* 321, 879–883.
8. Guarino, A., Cohen, M., Thompson, M., Dharmsathaphorn, K., and Giannella, R. (1987) *Am. J. Physiol.* 253, G775–G780.
9. Robins-Browne, R. M. (1987) *Rev. Infect. Dis.* 9, 28–53.
10. Levine, M. M. (1987) *J. Infect. Dis.* 155, 377–389.
11. Burgess, M. N., Bywater, R. J., Cowley, C. M., Mullan N. A. and Newsome D. M. *Infect. Immun.* 21, 526–531.
12. Steiner, A. L., Paghara, A. S., Chase, L. R., and Kipnis, D. M. (1972) *J. Biol. Chem.* 247, 1114–1120.
13. Hunkapiller, M. W., Hewick, R. M., Dreyer, R. J., and Hood, L. E. (1983) *Methods Enzymol.* 91, 399–413.
14. Kruft, V., Ulrike, K., and Wittmann-Liebold, B. (1991) *Anal. Biochem.* 193, 306–309.
15. Bruins, A. P., Covey, T. R., Henion, J. D. (1987) *Anal. Chem.* 59, 2642–2651.
16. Fraker, P., and Speck, J. C. (1978) *Biochem. Biophys. Res. Commun.* 80, 849–857.
17. Merrifield, R. B. (1963) *J. Am. Chem. Soc.* 85, 2149–2154.
18. Tam, J. P., Wu C. -R., Tiu, W., and Zhang, J.-W. (1991) *Twelfth American Peptide Symposium*, Abstract LW5.
9. Guzman-Verduzo, L. M., and Kupersztoch, Y. M. (1989) *Infect. Immun.* 57 645–648.
20. Houghten, R. A., Ostresh, J. M., and Klipstein, F. A. (1984) *Eur. J. Biochem.* 145, 157–162.
21. Krause, W. J., Freeman, R. H., and Forte, L. R. (1990) *Cell Tissue Res.* 260, 387–394.
22. Forte, L. R., Krause, W. J., and Freeman, R. H. (1988) *Am. J. Physiol.* 257, F1040–F1046.

SEQUENCE LISTING (1) GENERAL INFORMATION:

-continued
SEQUENCE LISTING (i) APPLICANT: Currie, Mark G
(ii) TITLE OF INVENTION: Pentadecapeptide, Guanylin, Which Stimulates Intestinal Guanylate Cyclase
(iii) NUMBER OF SEQUENCES: 1
(iv) CORRESPONDENCE ADDRESS:
  (A) ADDRESSEE: Scott J. Meyer
  (B) STREET: Monsanto Co. 800 N. Lindbergh Blvd., A3SD
  (C) CITY: St. Louis
  (D) STATE: MO
  (E) COUNTRY: USA
  (F) ZIP: 63141
(v) COMPUTER READABLE FORM:
  (A) MEDIUM TYPE: Floppy disk
  (B) COMPUTER: IBM PC compatible
  (C) OPERATING SYSTEM: PC-DOS/MS-DOS
  (D) SOFTWARE: PatentIn Release #1.0, Version #1.25
(vi) CURRENT APPLICATION DATA:
  (A) APPLICATION NUMBER: 07/764,461
  (B) FILING DATE: 9/23/91
  (C) CLASSIFICATION: 530/326
(viii) ATTORNEY/AGENT INFORMATION:
  (A) NAME: Meyer, Scott J
  (B) REGISTRATION NUMBER: 25,275
  (C) REFERENCE/DOCKET NUMBER: 07-21(808)A
(ix) TELECOMMUNICATION INFORMATION:
  (A) TELEPHONE: (314)694-3117
  (B) TELEFAX: (314)694-5435
(2) INFORMATION FOR SEQ IN NO:1:
  (i) SEQUENCE CHARACTERISTICS:
    (A) LENGTH: 15 amino acids
    (B) TYPE: amino acid
    (C) STRANDEDNESS: single
    (D) TOPOLOGY: linear
  (ii) MOLECULE TYPE: peptide
  (xi) SEQUENCE DESCRIPTION: SEQ ID NO:1:
Pro Asn Thr Cys Glu Ile Cys Ala Tyr Ala Ala Cys Thr Gly Cys
1           5               10              15

What is claimed is:
1. A substantially pure pentadecapeptide having the following amino acid sequence

Pro—Asn—Thr—Cys—Glu—Ile—Cys—Ala—Tyr—Ala—Ala—
1                           5                               10
Cys—Thr—Gly—Cys
              15 and having two disulfide bridges, one between Cys residues 4 and 12 and the other between Cys residues 7 and 15.

* * * * *